United States Patent [19]

Maze et al.

[11] Patent Number: 5,344,840
[45] Date of Patent: Sep. 6, 1994

[54] 4-SUBSTITUTED IMIDAZOLE DERIVATIVES USEFUL IN PERIOPERATIVE CARE

[75] Inventors: Mervyn Maze, Portola Valley, Calif.; Mika Scheinin, Naantali, Finland

[73] Assignee: Orion-Yhtyma OY, Turku, Finland

[21] Appl. No.: 3,681

[22] Filed: Jan. 13, 1993

Related U.S. Application Data

[60] Continuation of Ser. No. 884,288, May 15, 1992, abandoned, which is a continuation of Ser. No. 790,116, Nov. 12, 1991, abandoned, which is a continuation of Ser. No. 606,272, Oct. 31, 1990, abandoned, which is a division of Ser. No. 313,832, Feb. 23, 1989, abandoned.

[30] Foreign Application Priority Data

Feb. 29, 1988 [GB] United Kingdom ................ 8804683

[51] Int. Cl.$^5$ .......................................... A61K 31/415
[52] U.S. Cl. .................................................. 514/396
[58] Field of Search ................................. 514/356, 396

[56] References Cited

FOREIGN PATENT DOCUMENTS 0187471 7/1986 European Pat. Off. .
0270267 6/1988 European Pat. Off. .

OTHER PUBLICATIONS

Chemical Abstracts 105:183977c (1986).
Chemical Abstracts 107:51881y (1987).
Chemical Abstracts 108:16172s (1988) Abstracting Scheinin et al. Reference (1987).

Primary Examiner—Jerome D. Goldberg
Attorney, Agent, or Firm—Adduci, Mastriani, Schaumberg & Schill

[57] ABSTRACT

4-[1-(2,3-dimethylphenyl)ethyl]-1H-imidazole, known as medetomidine, and in particular its d-enantiomer and salts thereof are useful in perioperative care, in particular in reducing the amount of anaesthetic it is necessary to administer.

3 Claims, No Drawings

4-SUBSTITUTED IMIDAZOLE DERIVATIVES USEFUL IN PERIOPERATIVE CARE

This application is a continuation of application Ser. No. 07/884,288, filed May 15, 1992, which is a continuation of application Ser. No. 07/790,116, filed Nov. 12, 1991, which is a continuation of application Ser. No. 606,272, filed Oct. 31, 1990, which is a divisional of application Ser. No. 07/313,832 filed Feb. 23, 1989, now all abandoned.

This invention relates to perioperative use of racemic and dextro-4-[1(2,3-dimethylphenyl)ethyl]-1H-imidazole and their non-toxic pharmaceutically acceptable salts. In the presence of these 4-substituted imidazole compounds, less anesthetic agent is required to achieve a given level of surgical anesthesia. These compounds also decrease circulating catecholamines thereby reducing the stress to which the cardiovascular system is exposed in the perioperative period.

Racemic 4-[1-(2,3-dimethylphenyl)ethyl]-1H-imidazole, which is known under the name medetomidine and which has the formula

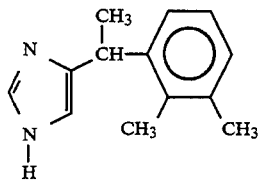

(I)

is a selective and potent $\alpha_2$-adrenoreceptor agonist. It has earlier been disclosed e.g. in the European Patent Publication No. 72615 as an antihypertensive agent and in the European Patent Publication No. 187471 as a veterinary sedative-analgesic agent.

It has further been observed that this compound also possesses anxiolytic effects and can therefore be used in the treatment of general anxiety, panic disorder and various kinds withdrawal symptoms.

As the compound of formula (I) possesses one asymmetric carbon atom this compound, which is a racemic mixture of two optcially acitve stereoisomers, can be split up into its d- and l-enantiomers. In particular the d-enantiomer has been found to exhibit surprisingly high selectively and potency as an $\alpha_2$-adrenoreceptor agonist.

Clonidine, a known antihypertensive drug (U.S. Pat. No. 3,202,660), has recently been reported to exhibit valuable properties for the use in the perioperative field. These observations have been reported in two papers: Flacke J W, Bloor B C, Flacke W E, Wong D, Dazza S, Stead, S W, Laks H: Reduced narcotic requirement by clonidine with improved hemodynamic and adrenergic stability in patients undergoing coronary bypass surgery; Anesthesiology 67:909–917, 1987 and Ghignone, M, Calvillo O, Quintin L: Anesthesia and hypertension: The effects of clonidine on perioperative hemodynamics and isoflurane requirements; Anesthesiology 67:901–908, 1987.

The first paper relates to a study of patients undergoing coronary artery bypass graft operations. Clonidine was given as premedication as well as intraoperatively. The administration of clonidine caused reduction in the anesthesia requirement and decreased plasma concentration of catecholamines. The second paper relates to a study of the influence of clonidine premedication on perioperative hemodynamics in hypertensive patients. Clonidine decreased the lability of heart rate and blood pressure in hypertensive patients and the requirement for anesthesia decreased by about 40%.

It has now been found that medetomidine and the d-enantiomer of 4-[1-(2,3-dimethylphenyl)ethyl]-1H-imidazole and their pharmaceutically acceptable salts exhibit properties which make them useful in the perioperative care of mammals. The d-enantiomer is especially useful in this respect.

Thus the present invention provides a compound which is racemic or dextro 4-[1-(2,3-dimethylphenyl)ethyl]-1H-imidazole or a non-toxic pharmaceutically acceptable salt thereof, for use in the manufacture of a medicament for perioperative treatment of mammals to reduce the responses of the autonomic nervous system to stressful stimuli during the operation.

The present invention also provides a pharmaceutical composition comprising dextro 4-[1-(2,3-dimethylphenyl)ethyl]-1H-imidazole or a non-toxic pharmaceutically acceptable salt thereof and a pharmaceutically acceptable carrier or diluent.

Medetomidine and its d-enantiomer essentially reduce the anesthetic requirement and other stress factors during the operation. The MAC-sparing (MAC=-minimum alveolar concentration) and cardiovascular effects of these compounds in halothane-anesthetized dogs are reported as follows: Anesthesia was induced by mask inhalation of halothane in oxygen in male beagles (8–11 kg). Following tracheal intubation, ventilation was controlled to maintain normocarbia ($CO_2$ $ET$—4.5%). Catheters were inserted percutaneously for: 1) intraarterial blood gas determination and pressure recording (femoral artery); 2) pulmonary arterial and central venous pressure monitoring and cardiac output (thermodiluation) assessment; and 3) intravenous fluid and drug administration. End-tidal halothane and $CO_2$ concentrations (infrared analysis), heart rate and rhythm (lead II of the EKG), systemic arterial pressure, central venous pressure, and pulmonary arterial pressure were continuously displayed and recorded. Core temperature was maintained at 37° C. with insulating blankets and heating lamps. After a 2 h equilibration period, the MAC for halothane was determined as previously described (Nicholls E A, Louis G L, Prokocimer P G, Maze M: Halothane anesthetic requirements are not affected by aminophylline treatment in rats and dogs. Anesthesiology 65:637–641, 1986) and baseline hemodynamic function (mean arterial blood pressure, heart rate, central venous pressure, pulmonary arterial diastolic pressure, pulmonary artery occluded pressure, cardiac output and derived systemic vascular resistance) was assessed. Medetomidine in the DL− (n−7), D− (n−5), and L-forms were administrated in separate experiments at each of three doses (1,3 and 10 μg/kg) via the right arterial port over 15 min while maintaing the dog at its individual MAC for halothane. Ten minutes after the termination of the infusion, (at which time the profile was stable) hemodynamic function was reassessed. Also at this time arterial blood was sampled for 1) measurement of gas tensions and acid/base status; and 2) circulating norepinephrine. MAC determination was then repeated following which the successive dose of medetomidine was given and the routine repeated. Data were compared by ANOVA for repeated measurements and subsequently by paired t-test with Bonferroni correction. A p value of <0.05 was considered the level for statistical significance. MAC for halothane significantly decreased following DL-medetomidine administration in a dose-dependent fashion to the extent that at the highest dose (10 μg/kg), the halothane MAC was less than <0.1%.

This effect could be mimicked by the D-isomer while the L-isomer was without effect. Neither isomer changed the mean arterial pressure while only the D-isomer significantly decreased heart rate and cardiac output.

Results

MAC for halothane significantly decreased following medetomidine administration in a dose-dependent fashion. The D-enantiomer displayed the same MAC-sparing effect (Table 1).

TABLE 1

Effect of medetomidine and the d-enantiomer on MAC

| Dose μg/kg | end-tidal halothane (% v/v) | |
|---|---|---|
| | medetomidine X ± SD (Standard deviation) | d-enantiomer X ± SD |
| 0 | 0.90 ± .07 | 1.00 ± .16 |
| 1 | 0.73 ± .21 | 0.65 ± .14 |
| 3 | 0.35 ± .19 | 0.40 ± .09 |
| 10 | 0.05 ± .09 | 0.11 ± .07 |

Table 2 and 3 disclose the decreased heart rate and cardiac output resulting from the administration of the compounds.

TABLE 2

Effect of medetomidine and the d-enantiomer on heart rate (beats per minute) at 1 MAC halothane

| Dose μg/kg | medetomidine X ± SD (bpm) | d-enantiomer X ± SD (bpm) |
|---|---|---|
| 0 | 111 ± 15 | 116 ± 6 |
| 1 | 89 ± 14 | 86 ± 9 |
| 3 | 76 ± 10 | 64 ± 9 |
| 10 | 63 ± 10 | 57 ± 6 |

TABLE 3

Effect of medetomidine and the d-enantiomer on cardiac output at 1 MAC halothane

| Dose μg/kg | medetomidine X ± SD (l/min) | d-enantiomer X ± SD (l/min) |
|---|---|---|
| 0 | 2.25 ± .85 | 2.61 ± .36 |
| 1 | 1.43 ± .53 | 1.71 ± .73 |

TABLE 3-continued

Effect of medetomidine and the d-enantiomer on cardiac output at 1 MAC halothane

| Dose μg/kg | medetomidine X ± SD (l/min) | d-enantiomer X ± SD (l/min) |
|---|---|---|
| 3 | 0.93 ± .22 | 1.07 ± .14 |
| 10 | 0.86 ± .25 | 0.97 ± .09 |

The compounds can be administered i.v., i.m., or orally The preferably dose range is 1 μg/kg–10 μg/kg.

Medetomidine as premedication before dental surgery.

Racemic medetomidine (50 μg, intravenously) was given to ten healthy subjects as premedication 20–30 min before surgical third molar extraction in a random-order, cross-over, placebo-controlled phase II clinical investigation. Local anaesthesia was with lidocaine/epinephrine. Each patient had two operations separated by at least three weeks. Medetomidine was rated as clearly superior to placebo by both the patients and the dental surgeon (see Table 4). No adverse effects were noted, neither in hemodynamic parameters, clinical chemistry tests nor in the patients' subjective reports.

TABLE 4

Effectiveness of medetomidine as premedication before surgical third molar extraction (10 patients, bilateral operations)

| | Racemic medetomidine better | both drugs equal | placebo better |
|---|---|---|---|
| Patients' preference | 8 | 2 | 0 |
| Effectiveness assessed by dental surgeon | 10 | 0 | 0 |

We claim:

1. A method of perioperative treatment of mammals to reduce the responses of the autonomic nervous system to stressful stimuli during an operation by administering to said mammal in whom such reduction is desired an effective amount of dextro 4-[1-(2,3-dimethylpheny)-ethyl] -1H-imidazole or a non-toxic pharmaceutically acceptable salt thereof substantially in the absence of the laevo form of said compound.

2. A method according to claim 1 wherein the compound is administered as anxiolytic analgesic premedication prior to an operation with or without the administration of an amount of anaesthetic sufficient to achieve a desired level of local or general anaesthesia.

3. A method according to claim 1 wherein the compound is administered preoperatively as sedative analgesic to potentiate the effect of an anaesthetic and thus to reduce the amount of anaesthetic required to achieve a desired level of anaesthesia.

* * * * *